(12) United States Patent
Chang

(10) Patent No.: US 9,096,880 B2
(45) Date of Patent: *Aug. 4, 2015

(54) SOLUBILITY ENHANCING PEPTIDE AND USE THEREOF

(71) Applicant: National Tsing Hua University, Hsinchu (TW)

(72) Inventor: Margaret Dah-Tsyr Chang, Taipei (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/275,903

(22) Filed: May 13, 2014

(65) Prior Publication Data

US 2014/0342400 A1    Nov. 20, 2014

Related U.S. Application Data

(60) Provisional application No. 61/823,531, filed on May 15, 2013.

(51) Int. Cl.
| | | |
|---|---|---|
| C12P 21/02 | (2006.01) |
| C07K 14/435 | (2006.01) |
| C12N 15/62 | (2006.01) |
| C12P 21/04 | (2006.01) |
| C12N 15/00 | (2006.01) |
| C12N 15/64 | (2006.01) |
| C07H 21/04 | (2006.01) |
| C07K 14/00 | (2006.01) |

(52) U.S. Cl.
CPC ............ *C12P 21/02* (2013.01); *C07K 14/00* (2013.01); *C07K 14/001* (2013.01); *C07K 14/43509* (2013.01); *C12N 15/62* (2013.01); *C07K 2319/33* (2013.01); *C07K 2319/35* (2013.01)

(58) Field of Classification Search
None
See application file for complete search history.

(56) References Cited

U.S. PATENT DOCUMENTS 8,664,475 B2 *   3/2014   Puzio et al. .................. 800/278

* cited by examiner

*Primary Examiner* — Celine Qian
*Assistant Examiner* — Nancy J Leith
(74) *Attorney, Agent, or Firm* — Hannah M. Tien

(57) ABSTRACT

The present invention relates to an isolated peptide consisting of the amino acid sequence of SEQ ID NO: 1. The present invention also relates to a method for increasing expression of a target protein using the peptide consisting of the amino acid sequence of SEQ ID NO: 1, comprising (a) fusing the peptide with the target protein to form a recombinant protein; and (b) expressing the recombinant protein by an expression host.

12 Claims, 4 Drawing Sheets

```
eRNase_HUMAN    RPPQFTRAQWFAIQHISLNPPRCTIAMRAINNYRWRCKNQNTFLRTTFAN 50
eRNase_PANTR    RPPQFTRAQWFAIQHISLNPPRCTIAMRVINNYRWRCKNQNTFLRTTFAN 50
eRNase_GORGO    RPPQFTRAQWFAIQHISLNPPRCTIAMRVINNYRWRCKNQNTFLRTTFAN 50
eRNase_MACFA    RPPQFTKAQWFAIQHINVNPPRCTIAMRVINNYQRRCKNQNTFLRTTFAY 50
eRNase_MACNE    RPPQFTKAQWFAIQHINVNPPRCTIAMRVINNYQRRCKNQNTFLRTTFAN 50
eRNase_PONPY    KPRQFTRAQWFAIQHVSLNPPQCTTAMRVINNYQRRCKDQNTFLRTTFAN 50
                 * *   :.:.. :*.  .*:: *:* ** eRNase_HUMAN    VVNVCGNQSIRCPHNRTLNNCHRSRFRVPLLHCDLINPGAQNISNCTYAD 100
eRNase_PANTR    VVNVCGNQSIRCPHNRTLNNCHQSRFRVPLLHCDLINPGAQNISNCRYAD 100
eRNase_GORGO    VVNVCGNQSIRCLHNRTLNNCHRSRFRVPLLHCDLINPGAQNISNCRYAD 100
eRNase_MACFA    TANVCRNERIRCPRNRTLHNCHRSRYRVPLLHCDLINPGAQNISTCRYAD 100
eRNase_MACNE    TVNVCRNRSIRCPRNRTLHNCHRSSYRVPLLHCDLINPGAQNISTCRYAD 100
eRNase_PONPY    VVNVCGNPNITCPRNRTLHNCHRSRFQVPLLHCNLINPGAQNISNCKYAD 100
                 ..:** *  : *   * : :***:*  :***:**:* .*. :.**.* *::

eRNase_HUMAN    RPGRRFYVVACDNRDP-RDSPRYPVVPVHLDTTI 133
eRNase_PANTR    RPGRRFYVVACDNRDP-RDSPRYPVVPVHLDATI 133
eRNase_GORGO    RPGRRFYVVACDNRDP-QDSPRYPVVPVHLDTTI 133
eRNase_MACFA    RPGRRFYVVACESRDP-RDSPRYPVVPVHLDTTI 133
eRNase_MACNE    RPGRRFYVVACESRDP-RDSPRYPVVPVHLDTII 133
eRNase_PONPY    RTERRFYVVACDNRDP-RDSPRYPVVPVHLDTTI 133
                 . . :*:***:. *  :*.*:********* *
```

SOLUBILITY ENHANCING PEPTIDE AND USE THEREOF

CROSS-REFERENCES TO RELATED APPLICATIONS

The present application is a regular application which claims priority to U.S. Provisional Application No. 61/823,531, filed on May 15, 2013, incorporated herein by reference in its entirety.

FIELD OF THE INVENTION

The present invention relates to an artificial peptide and use thereof.

The sequence listing text file, file name 2298_NTHU_SQlist_ST25, created May 9, 2014, file size 17,869 bytes, is incorporated herein by reference in its entirety.

BACKGROUND OF THE INVENTION

The supply of many valuable proteins that have potential clinical or industrial use is often limited by their low natural availability. With the modern advances in genomics, proteomics and bioinformatics, the number of proteins being produced using recombinant techniques is exponentially increasing and seems to guarantee an unlimited supply of recombinant proteins. However, the soluble expression of heterologous proteins in *E. coli* remains a serious bottleneck in protein production. Overexpression of cloned genes in *E. coli* may lead to the formation of intracellular proteinaceous granules that are readily visible under the light microscope. A number of parameters relating to the host cell, the growth conditions and the properties of the particular protein affect this process. Therefore, new technologies to enhance protein expression and simplify the purification process are needed to help protein investigation at the scale of many proteins simultaneously.

BRIEF DESCRIPTION OF THE DRAWINGS

FIG. 4 shows primary sequence alignment of six kinds of mature eosinophil RNase sequences originated from different primates, including *Homo sapiens, Pantroglodytes, Gorilla Gorilla, Macaca fascicularis, Macaca nemestrina,* and *Pongo pygmaeus.* Primate eosinophil RNase sequences were extracted from NCBI database. Sequences are aligned using Clustal X2. Fully conserved amino acids are indicated by asterisk (*), highly similar amino acids are indicated by colon (:), and weakly similar amino acids are indicated by dot (.). eRNase_HUMAN means human eosinophil RNase (SEQ ID NO: 9); eRNase_PANTR means *Pan troglodytes* eosinophil RNase (SEQ ID NO: 14); eRNase_GORGO means *Gorilla Gorilla* eosinophil RNase (SEQ ID NO: 15); eRNase_MACFA means *Macaca fascicularis* eosinophil RNase (SEQ ID NO: 16); eRNase_MACNE means *Macaca nemestrina* eosinophil RNase (SEQ ID NO: 17); and eRNase_PONPY means *Pongo pygmaeus* eosinophil RNase (SEQ ID NO: 18).

SUMMARY OF THE INVENTION

Figure 1:
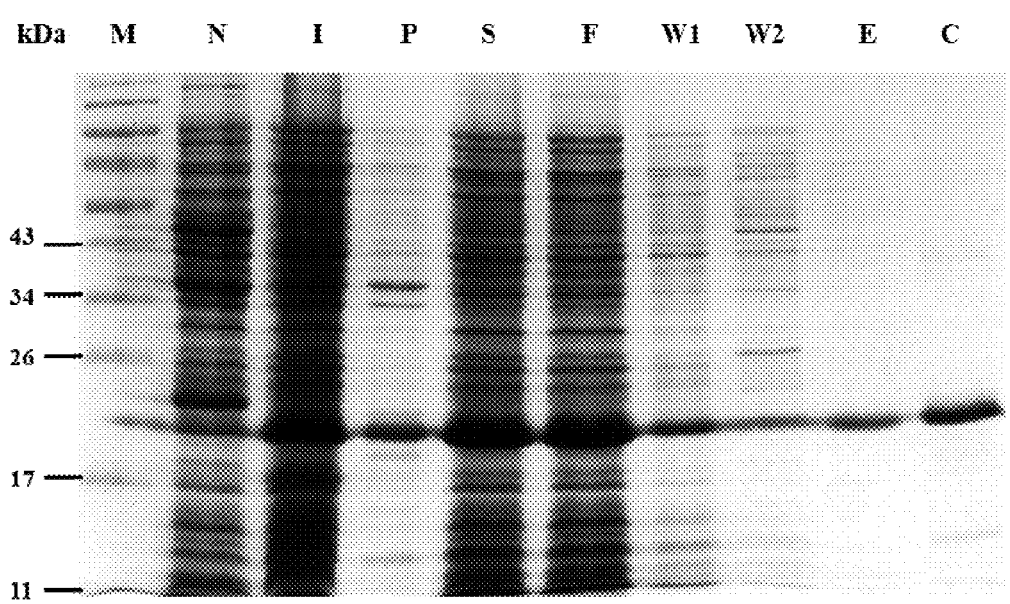
FIG. 1 shows purification and characterization of recombinant bacteria recognizing lectin (rBRL). After induction with 0.1 mM IPTG at 16° C. for 16 h, the supernatant of cell lysate containing rBRL is collected by centrifugation and subjected to Nickel column chromatography for purification. Aliquots of each fraction are analyzed by 15% (w/v) SDS-PAGE. Lane M: molecular weight marker; Lane N: cell lysate of *E. coli* without IPTG induction; Lane I: cell lysate of *E. coli* with IPTG induction; Lane P: insoluble pellet; Lane S: supernatant; Lane F: binding flow-through; Lane W1: washing fraction with 20 mM Tris-HCl, 200 mM NaCl, 5 mM imidazole; Lane W2: washing fraction with 20 mM Tris-HCl, 200 mM NaCl, 50 mM imidazole; Lane E: eluting fraction with 20 mM Tris-HCl, 200 mM NaCl, 300 mM imidazole; Lane C: concentrated fraction.

The present invention relates to an isolated peptide consisting of the amino acid sequence of SEQ ID NO: 1. The present invention also relates to a method for increasing expression of a target protein by using the peptide consisting of the amino acid sequence of SEQ ID NO: 1, comprising (a) fusing the peptide with the target protein to form a recombinant protein; and (b) expressing the recombinant protein by an expression host.

DETAILED DESCRIPTION OF THE INVENTION

Fusion protein approach may overcome the low expression obstacle using affinity tags for increasing protein expression, and aiding in protein purification efficiency.

An artificial peptide was designed to increase solubility of a target fusion protein. An example of the amino acid sequence of such artificial peptide includes but is not limited to SKPTTTTTTTTTAPSTSTTTRPSSSEPATFPTGDSTISS (SEQ ID NO: 1).

Horseshoe crab bacteria recognizing lectin (BRL) derived from hemocyte of Taiwanese *Tachypleus tridentatus* is a LPS-binding protein isolated from plasma. An example of the amino acid sequence of BRL includes but is not limited to (SEQ ID NO: 2)
EDDCTCVTDRSLEGKLMKHPSTPAVYQILDGCRRLVPNPPTYNNIYKNW

ECIQSNILEKLLCKCDSLSNGAELIKGSGDTVYLLSNGVKRPIADPETF

NGFCFDWNKIKTYSDIVINSLSTGPIIIIK.

Human eosinophil ribonuclease (RNase) belongs to RNase A superfamily and is secreted by eosinophil during inflammation. Primate eosinophil RNase sequences were extracted from NCBI database and aligned with human eosinophil RNase (FIG. 4). Human eosinophil RNase shows high degree of similarity to primate eosinophil RNases (higher than 86% sequence identity). Human eosinophil RNase is composed of 133 amino acids with isoelectricpoint of 10.8. An example of the amino acid sequence of human eosinophil RNase includes but is not limited to (SEQ ID NO: 9)
RPPQFTRAQWFAIQHISLNPPRCTIAMRAINNYRWRCKNQNTFLRTTFA

NVVNVCGNQSIRCPHNRTLNNCHRSRFRVPLLHCDLINPGAQNISNCTY

ADRPGRRFYVVACDNRDPRDSPRYPVVPVHLDTTI.

In this invention, a novel recombinant protein rBRL comprising an N-terminal 39-amino acid artificial peptide and a C-terminal 128-amino acid BRL, (for example: MSKPTTTTTTTTTAPSTSTTTRPSSSE-PATFPTGDSTISSEFEDDCTCVTDRSLEG KLMKHPST-PAVYQILDGCRRLVPNPPTYNNIYKNWE-CIQSNILEKLLCKCDSLS NGAELIKGSGDTVYLLSNGVKRPIAD-PETFNGFCFDWNKIKTYSDIVINSLSTG PIIIIKHHH-HHH (SEQ ID NO: 3)), has been created in *E. coli* expression system. The 1$^{st}$ amino acid residue (M) and the 41$^{th}$ to 42$^{th}$ amino acid residues (EF) of SEQ ID NO: 3 are residues derived from vector pET23a and may be altered when different vector is used, even can be absent in one aspect of the present invention. In addition, the 6 residues at the end of SEQ ID NO: 3 (HHHHHH) functions as a tag for purification and can be replaced by any other sequence having similar function, even can be absent in one aspect of the present invention. According the above, it is noted that the present invention also provides a kind of rBRL which consists of the amino acid sequence of SEQ ID NO: 4 (SKPTTTTTTTTTAPST-STTTRPSSSEPATFPTGDSTISSEDDCTCVTDRSLEGKL MKHPSTPAVYQILDGCRRLVPNPPTYN-NIYKNWECIQSNILEKLLCKCDSLSNG AELIKGS-GDTVYLLSNGVKRPIADPETFNGFCFD-WNKIKTYSDIVINSLSTGPIII IK).

In this study, a novel recombinant protein recombinant eosinophil ribonuclease (reRNase) comprising an N-terminal 39-amino acid artificial peptide and a C-terminal 133-amino acid human eosinophil RNase, (for example: MSKPTTTTTTTTTAPSTSTTTRPSSSE-PATFPTGDSTISSEFRPPQFTRAQWFAIQ HISLNPPRC-TIAMRAINNYRWRCKNQNTFLRTTFANV-VNVCGNQSIRCPHNRT LNNCHRSRFRVPLLHCDLINP-GAQNISNCTYADRPGRRFYVVACDNRDPRDS PRYPV-VPVHLDTTIHHHHHH (SEQ ID NO: 10)), has been created in *E. coli* expression system. The 1$^{st}$ amino acid residue (M) and the 41$^{th}$ to 42$^{th}$ amino acid residues (EF) of SEQ ID NO: 10 are residues derived from vector pET23a and may be altered when different vector is used, even can be absent in one aspect of the present invention. In addition, the 6 residues at the end of SEQ ID NO: 10 (HHHHHH) functions as a tag for purification and can be replaced by any other sequence having similar function, even can be absent in one aspect of the present invention. According the above, it is noted that the present invention also provides a kind of reRNase which consists of the amino acid sequence of SEQ ID NO: 11 (SKPTTTTTTTTTAPSTSTTTRPSSSEPA-TFPTGDSTISSRPPQFTRAQWFAIQHIS LNPPRCTIAM-RAINNYRWRCKNQNTFLRTTFANVVN-VCGNQSIRCPHNRTLN NCHRSRFRVPLLHCDLINP-GAQNISNCTYADRPGRRFYVVACDNRDPRDSPR YPV-VPVHLDTTI).

It is noted that any mutation of the above amino acid sequences with the similar activities is involved in the scope of the present invention.

Addition of the artificial peptide (SEQ ID NO: 1) successfully enhances BRL or eosinophil RNase expression as well as simplifies the purification process.

The terms used in the description herein will have their ordinary and common meaning as understood by those skilled in the art, unless specifically defined otherwise.

Thus, the present invention provides an isolated peptide consisting of the amino acid sequence of SEQ ID NO: 1. The present invention also provides a method for increasing expression of a target protein by using an isolated peptide consisting of the amino acid sequence of SEQ ID NO: 1, comprising (a) fusing the peptide with the target protein to form a recombinant protein; and (b) expressing the recombinant protein by an expression host. Preferably, the target protein is a glycan binding protein; more preferably, the target protein is a vertebrate plasma lectin or a vertebrate ribonuclease; still more preferably, the target protein is a bacteria recognizing lectin or a primate eosinophil ribonuclease; still more preferably, the target protein is a human eosinophil ribonuclease. In an embodiment, the expression host is a bacterium, a yeast, an insect cell or a mammalian cell. More preferably, the bacterium is *Escherichia coli*. The method not only simplifies the purification process for the target protein but also retains activity of the target protein after fusing the peptide to the target protein.

EXAMPLES

The examples below are non-limiting and are merely representative of various aspects and features of the present invention.

Example 1

Materials and Methods

Reagents

*E. coli* Top10F' (Invitrogen) was used for vector construction and DNA manipulation, *E. coli* expression strain ROSETTA™ (DE3) (Stratagene), vectors pET23a purchased from NOVAGEN® were used for protein expression. All other buffers and reagents are of the highest commercial purity.

Protein Expression and Purification

DNA fragment encoding SEQ ID NO: 1 was amplified by PCR with primers 5' NdeI-ANP (5' CATATGTCCAAGC-CACTACTACTAC 3') (SEQ ID NO: 5) and 3' EcoRI-ANP (5' GAATTCTGAGGAGATTGTAGAGTCACC 3') (SEQ ID NO: 6). DNA fragment encoding BRL (SEQ ID NO: 2) was amplified by PCR using cDNA which reverse transcribed from *Tachypleus tridentatus*' RNA as template. Primers 5' EcoRI-BRL (5' GAATTCGAAGATGACTGCACGTGA-CAGAC 3') (SEQ ID NO: 7) and 3' NotI-BRL-6His (5' GCG-GCCGCTTAATGATGATGATGATGATGC TTAATTAT-TATAATAGGTCC 3') (SEQ ID NO: 8) were used for PCR procedure. Two purified PCR products were digested with NdeI/EcoRI and EcoRI/NotI respectively, ligated with pET23a treated with same restriction enzymes.

The recombinant plasmid was confirmed by sequencing and then transformed to *E. coli* Top1OF' and selected on agar plate containing 100 μg/ml Ampicillin. A single colony was picked on the selection plate and grown in 5 ml of Luria-Bertani (LB) medium (1% tryptone, 0.5% yeast extract, and 0.5% sodium chloride) containing the same concentration of the antibiotic at 37° C. overnight for plasmid extraction. The extracted plasmid was then transformed into *E. coli* expression strain ROSETTA™ (DE3) and selected on agar plate containing 100 μg/ml Ampicillin. A single colony was picked and grown in 1 L LB medium at 37° C. until $OD_{600}$ reached 0.4 to 0.6. Protein expression was induced by addition of IPTG to a final concentration of 0.1 mM and incubation at 16° C. for 16 h. Cells were harvested by centrifugation at 4000×g for 10 min at 4° C., and washed once with PBS. Then, cell pellet was resuspended in 50 mL of equilibrium buffer (20 mM Tris-HCl, 200 mM NaCl, 5 mM imidazole, pH 7.4) supplemented with protease inhibitor (1 mM phenylmethylsulfonyl fluoride, PMSF) and disrupted by a 3 cycles through a cell homogenizer (EMULSIFLEX®-C3 homogenizer) at 15,000 psi. The cell lysate was separated into supernatant and pellet by centrifugation at 16000×g for 30 min at 4° C. to remove cellular debris. The supernatant was subjected to purification by NI SEPHAROSE™ 6 Fast Flow (GE healthcare) column chromatography. The column was first pre-equilibrated with equilibrium buffer and at the end of sample loading, washed with 50 mL equilibrium buffer (W1) and 50 mL wash buffer (20 mM Tris-HCl, 200 mM NaCl, 50 mM imidazole, pH 7.4) (W2). To recover bound protein, the column was eluted with elution buffer (20 mM Tris-HCl, 200 mM NaCl, 300 mM imidazole, pH 7.4). The eluted rBRL was then concentrated and buffer-exchanged to Tris buffer (20 mM Tris-HCl, 200 mM NaCl, pH 7.4).

Figure 2:
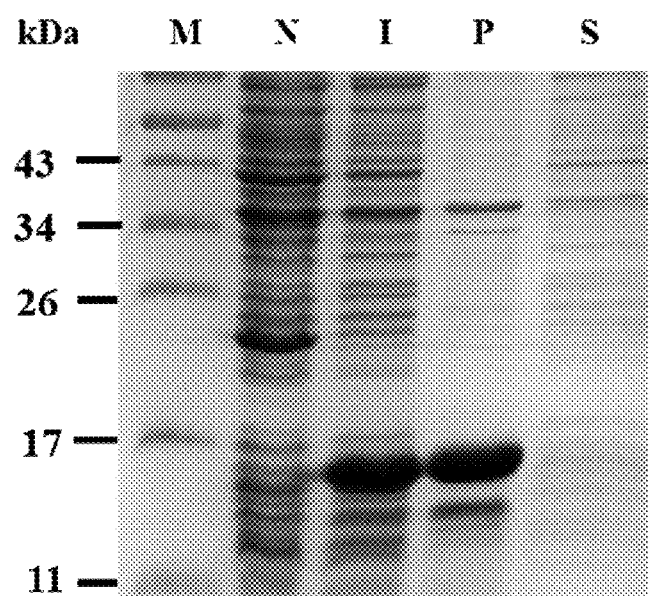
FIG. 2 shows small-scale expression of rBRL (N7) and rBRL (C7). Expression of (A) rBRL (N7) and (B) rBRL (C7) are induced by addition of 0.1 mM IPTG to the cultures and incubation at 16° C. for 16 h. Twenty microliters sample of each fraction is separated by 15% (w/v) SDS-PAGE and stained with Coomassie blue. Lane M: molecular weight marker; Lane N: cell lysate of *E. coli* without IPTG induction; Lane I: cell lysate of *E. coli* with IPTG induction; Lane P: insoluble pellet; Lane S: supernatant.
Figure 2:
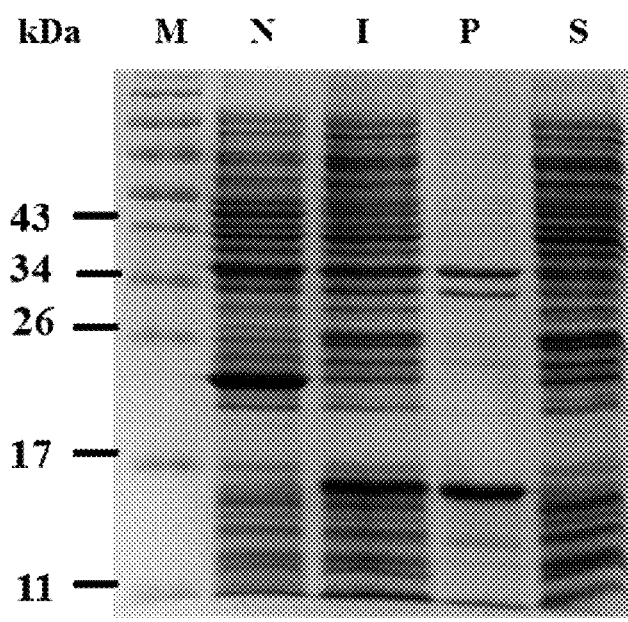

Results
Expression and Purification of rBRL rBRL was composed of an artificial N-terminal peptide and a C-terminal horseshoe crab bacteria recognizing lectin (BRL) derived from *T. tridentatus*. DNA fragments encoding artificial peptide and BRL were separately ligated into pET23a vector and the recombinant plasmid was transformed into *E. coli* ROSETTA™ (DE3) for protein expression. From 1 L of culture medium, approximately 6 mg of purified rBRL was obtained by Nickel column chromatography, with a recovery rate of 80.6% (FIG. 1). Five-fold higher yield of rBRL than BRL-6His has been achieved; indicating that the artificial peptide fused at the N-terminal end of BRL has successfully facilitated the isolation of rBRL. To further investigate the importance of the artificial peptide in BRL expression, a shorter peptide consisted of first and last 7 amino acids of the peptide were separately fused at the N-terminus of BRL (rBRL(N7) and rBRL(C7), respectively). The expression status revealed that BRL fused with both peptides were expressed in the inclusion body fraction, strongly indicated that full-length artificial peptide was required for soluble rBRL expression (FIGS. 2A and 2B, lane P).

Example 2

Materials and Methods

Reagents

*E. coli* Top10F' (Invitrogen) was used for vector construction and DNA manipulation, *E. coli* expression strain ROSETTA™ (DE3) (Stratagene), vectors pET23a purchased from NOVAGEN® were used for protein expression. All other buffers and reagents are of the highest commercial purity.

Protein Expression and Purification

DNA fragment encoding SEQ ID NO: 1 was amplified by PCR with primers 5' NdeI-ANP (5' CATATGTCCAAGC-CACTACTACTAC 3') (SEQ ID NO: 5) and 3' EcoRI-ANP (5' GAATTCTGAGGAGATTGTAGAGTCACC 3') (SEQ ID NO: 6). DNA fragment encoding human eosinophil RNase (SEQ ID NO: 9) was amplified from cDNA which reverse transcribed from asthma patient's RNA. PCR primers 5' EcoRI-RNase (5' GAATTCAGACCCCCACAGTTTAC-GAGG 3') (SEQ ID NO: 12) and 3' BamHI-RNase-6His (5' GGATTCTTAGTGGTGGTGGTGGTGGTG-GATGGTGGTATCCAGGTG 3') (SEQ ID NO: 13) was used for human eosinophil RNase amplification. PCR product encoding SEQ ID NO: 1 and human eosinophil RNase were digested with NdeI/EcoRI and EcoRI/BamHI respectively, ligated with pET23a treated with same restriction enzymes.

The recombinant plasmid was confirmed by sequencing and then transformed to *E. coli* Top10F' and selected on agar plate containing 100 μg/ml Ampicillin. A single colony of each clone was picked on the selection plate and grown in 5 ml of Luria-Bertani (LB) medium (1% tryptone, 0.5% yeast extract, and 0.5% sodium chloride) containing the same concentration of the antibiotic at 37° C. overnight for plasmid extraction. The extracted plasmid was then transformed into *E. coli* expression strain ROSETTA™ (DE3) and selected on agar plate containing 100 μg/ml Ampicillin. A single colony was picked and grown in 1 L LB medium at 37° C. until $OD_{600}$ reached 0.4 to 0.6. Protein expression was induced by addition of IPTG to a final concentration of 0.1 mM and incubation at 16° C. for 16 h. Cells were harvested by centrifugation at 4000×g for 10 min at 4° C., and washed once with PBS. Then, cell pellet was resuspended in buffer A (10 mM sodium phosphate buffer, 1 mM EDTA, pH 7.0) supplemented with protease inhibitor (1 mM phenylmethylsulfonyl fluoride, PMSF) and disrupted by 5 cycles of homogenization at 15,000 psi. After homogenization, the slurry was centrifuged at 16,000×g for 30 min at 4° C. to remove cellular debris. Protein in the supernatant was loaded onto a 5 mL HITRAP™ Heparin HP on a FPLC system (GE Health) with a flow rate of 2 mL/min, washed with buffer A until the OD280 absorbance reached the baseline then proteins were eluted with a linear NaCl gradient (0-2M NaCl). Fractions of each were analyzed by 15% (w/v) SDS-PAGE.

Figure 3:
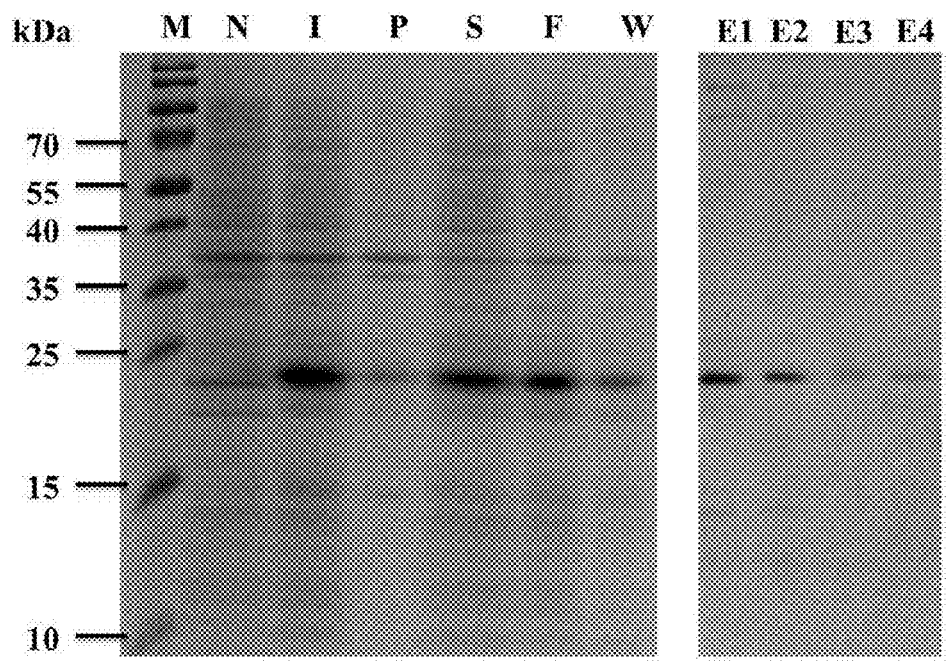
FIG. 3A shows purification and characterization of recombinant human eosinophil ribonuclease (reRNase). After induction with 0.1 mM IPTG at 16° C. for 16 h, the supernatant of cell lysate containing reRNase is collected by centrifugation and subjected to Heparin column chromatography for purification. Aliquots of each fraction are analyzed by 15% (w/v) SDS-PAGE. Lane M: molecular weight marker; Lane N: cell lysate of *E. coli* without IPTG induction; Lane I: cell lysate of *E. coli* with IPTG induction; Lane P: insoluble pellet; Lane S: supernatant; Lane F: binding flow-through; Lane W: washing fraction with 10 mM sodium phosphate buffer, 1 mM EDTA, E1~E4: eluting fraction with 10 mM sodium phosphate buffer, 1 mM EDTA, 0-2M NaCl.
FIG. 3B shows small-scale expression of RNase 3. Without an artificial peptide, reRNase major present in insoluble pellet after induction with 0.1 mM IPTG at 16° C. for 16 h.
Figure 3:
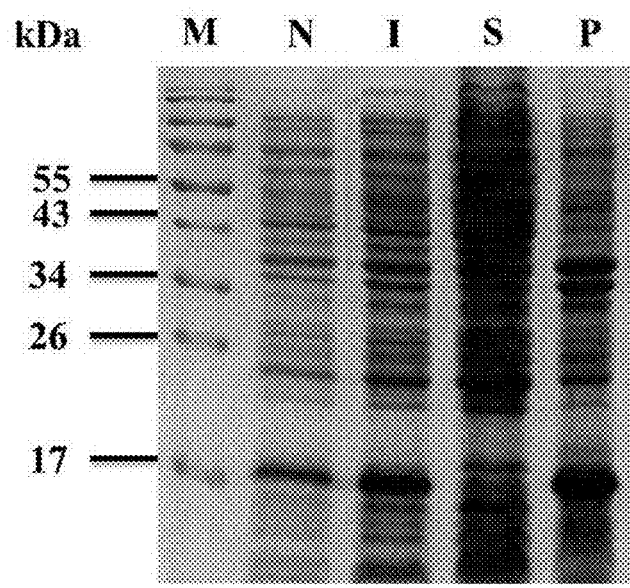

Results
Expression and Purification of reRNase reRNase was composed of an artificial N-terminal peptide and a C-terminal human eosinophil ribonuclease. DNA fragments encoding artificial peptide and human eosinophil RNase were separately ligated into pET23a vector and the recombinant plasmid was transformed into *E. coli* ROSETTA™ (DE3) for protein expression. The results showed that reRNase of expected molecular weight of 20.5 kDa was successfully expressed in *E. coli* BL21 ROSETTA™ (DE3) and most of the overexpressed protein was present in supernatant fraction (FIG. 3A, lane S). The soluble reRNase in supernatant fraction was then purified by HITRAP™ Heparin HP column on FPLC system. FIG. 3A (lane E1 and E2) showed that reRNase could be successfully eluted by a stepwise NaCl gradient. On the other hand, the expression of human eosinophil RNase without an artificial peptide (FIG. 3B) was mainly present in inclusion body (pellet fraction) as previously described.

One skilled in the art readily appreciates that the present invention is well adapted to carry out the objects and obtain the ends and advantages mentioned, as well as those inherent therein. The peptide/recombinant protein, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An artificial peptide consisting of the amino acid sequence of SEQ ID NO: 1, wherein said peptide can increase solubility of a target fusion protein.

2. A method for increasing expression of a target protein by using the peptide of claim 1, comprising (a) fusing a nucleic acid encoding the peptide of claim 1 with a nucleic acid encoding a target protein to form a recombinant nucleic acid; (b) transforming an expression host cell with the recombinant nucleic acid; and (c) expressing the recombinant nucleic acid in the expression host cell to form a target fusion protein, wherein expression of the target protein is increased.

3. The method of claim 2, wherein the target protein is a glycan binding protein.

4. The method of claim 3, wherein the target protein is a vertebrate plasma lectin.

5. The method of claim 4, wherein the target protein is a bacteria recognizing lectin.

6. The method of claim 3, wherein the target protein is a vertebrate ribonuclease.

7. The method of claim 6, wherein the target protein is a primate eosinophil ribonuclease.

8. The method of claim 6, wherein the target protein is a human eosinophil ribonuclease.

9. The method of claim 2, wherein the expression host cell is a bacterium, a yeast, an insect cell or a mammalian cell.

10. The method of claim 9, wherein the bacterium is *Escherichia coli*.

11. The method of claim 2, further comprising purifying the target protein.

12. The method of claim 2, wherein the target fusion protein retains the activity of the target protein.

* * * * *

SEQUENCE LISTING

```
<160> NUMBER OF SEQ ID NOS: 18

<210> SEQ ID NO 1
<211> LENGTH: 39
<212> TYPE: PRT
<213> ORGANISM: Artificial Sequence
<220> FEATURE:
<223> OTHER INFORMATION: Solubility enhancing peptide.
<220> FEATURE:
<221> NAME/KEY: PEPTIDE
<222> LOCATION: (1)..(39)

<400> SEQUENCE: 1

Ser Lys Pro Thr Thr Thr Thr Thr Thr Thr Thr Thr Ala Pro Ser Thr
1               5                   10                  15

Ser Thr Thr Thr Arg Pro Ser Ser Ser Glu Pro Ala Thr Phe Pro Thr
            20                  25                  30

Gly Asp Ser Thr Ile Ser Ser
        35

<210> SEQ ID NO 2
<211> LENGTH: 128
<212> TYPE: PRT
<213> ORGANISM: Tachypleus tridentatus
<220> FEATURE:
<221> NAME/KEY: mat_peptide
<222> LOCATION: (1)..(128)

<400> SEQUENCE: 2

Glu Asp Asp Cys Thr Cys Val Thr Asp Arg Ser Leu Glu Gly Lys Leu
1               5                   10                  15

Met Lys His Pro Ser Thr Pro Ala Val Tyr Gln Ile Leu Asp Gly Cys
            20                  25                  30

Arg Arg Leu Val Pro Asn Pro Pro Thr Tyr Asn Asn Ile Tyr Lys Asn
        35                  40                  45

Trp Glu Cys Ile Gln Ser Asn Ile Leu Glu Lys Leu Leu Cys Lys Cys
    50                  55                  60

Asp Ser Leu Ser Asn Gly Ala Glu Leu Ile Lys Gly Ser Gly Asp Thr
65                  70                  75                  80

Val Tyr Leu Leu Ser Asn Gly Val Lys Arg Pro Ile Ala Asp Pro Glu
                85                  90                  95

Thr Phe Asn Gly Phe Cys Phe Asp Trp Asn Lys Ile Lys Thr Tyr Ser
            100                 105                 110

Asp Ile Val Ile Asn Ser Leu Ser Thr Gly Pro Ile Ile Ile Ile Lys
        115                 120                 125
```

<210> SEQ ID NO 3
<211> LENGTH: 176
<212> TYPE: PRT
<213> ORGANISM: Artificial Sequence
<220> FEATURE:
<223> OTHER INFORMATION: A novel recombinant protein rBRL comprising an
     N-terminal 39-amino acid artificial peptide and a C-terminal
     128-amino acid BRL.
<220> FEATURE:
<221> NAME/KEY: MISC_FEATURE
<222> LOCATION: (1)..(176)

<400> SEQUENCE: 3

Met Ser Lys Pro Thr Thr Thr Thr Thr Thr Thr Thr Ala Pro Ser
1               5                   10                  15

Thr Ser Thr Thr Thr Arg Pro Ser Ser Ser Glu Pro Ala Thr Phe Pro
                20                  25                  30

Thr Gly Asp Ser Thr Ile Ser Ser Glu Phe Glu Asp Asp Cys Thr Cys
            35                  40                  45

Val Thr Asp Arg Ser Leu Glu Gly Lys Leu Met Lys His Pro Ser Thr
50                  55                  60

Pro Ala Val Tyr Gln Ile Leu Asp Gly Cys Arg Arg Leu Val Pro Asn
65                  70                  75                  80

Pro Pro Thr Tyr Asn Asn Ile Tyr Lys Asn Trp Glu Cys Ile Gln Ser
                85                  90                  95

Asn Ile Leu Glu Lys Leu Leu Cys Lys Cys Asp Ser Leu Ser Asn Gly
                100                 105                 110

Ala Glu Leu Ile Lys Gly Ser Gly Asp Thr Val Tyr Leu Leu Ser Asn
            115                 120                 125

Gly Val Lys Arg Pro Ile Ala Asp Pro Glu Thr Phe Asn Gly Phe Cys
130                 135                 140

Phe Asp Trp Asn Lys Ile Lys Thr Tyr Ser Asp Ile Val Ile Asn Ser
145                 150                 155                 160

Leu Ser Thr Gly Pro Ile Ile Ile Ile Lys His His His His His His
                165                 170                 175

<210> SEQ ID NO 4
<211> LENGTH: 167
<212> TYPE: PRT
<213> ORGANISM: Artificial Sequence
<220> FEATURE:
<223> OTHER INFORMATION: An alternative kind of rBRL.
<220> FEATURE:
<221> NAME/KEY: MISC_FEATURE
<222> LOCATION: (1)..(167)

<400> SEQUENCE: 4

Ser Lys Pro Thr Thr Thr Thr Thr Thr Thr Thr Ala Pro Ser Thr
1               5                   10                  15

Ser Thr Thr Thr Arg Pro Ser Ser Ser Glu Pro Ala Thr Phe Pro Thr
                20                  25                  30

Gly Asp Ser Thr Ile Ser Ser Glu Asp Asp Cys Thr Cys Val Thr Asp
            35                  40                  45

Arg Ser Leu Glu Gly Lys Leu Met Lys His Pro Ser Thr Pro Ala Val
50                  55                  60

Tyr Gln Ile Leu Asp Gly Cys Arg Arg Leu Val Pro Asn Pro Pro Thr
65                  70                  75                  80

Tyr Asn Asn Ile Tyr Lys Asn Trp Glu Cys Ile Gln Ser Asn Ile Leu
                85                  90                  95

Glu Lys Leu Leu Cys Lys Cys Asp Ser Leu Ser Asn Gly Ala Glu Leu
            100                 105                 110

Ile Lys Gly Ser Gly Asp Thr Val Tyr Leu Leu Ser Asn Gly Val Lys
        115                 120                 125

Arg Pro Ile Ala Asp Pro Glu Thr Phe Asn Gly Phe Cys Phe Asp Trp
    130                 135                 140

Asn Lys Ile Lys Thr Tyr Ser Asp Ile Val Ile Asn Ser Leu Ser Thr
145                 150                 155                 160

Gly Pro Ile Ile Ile Ile Lys
                165

<210> SEQ ID NO 5
<211> LENGTH: 25
<212> TYPE: DNA
<213> ORGANISM: Artificial Sequence
<220> FEATURE:
<223> OTHER INFORMATION: Primer 5' NdeI-ANP.
<220> FEATURE:
<221> NAME/KEY: primer_bind
<222> LOCATION: (1)..(25)

<400> SEQUENCE: 5
catatgtcca agccactact actac                                           25

<210> SEQ ID NO 6
<211> LENGTH: 27
<212> TYPE: DNA
<213> ORGANISM: Artificial Sequence
<220> FEATURE:
<223> OTHER INFORMATION: Primer 3' EcoRI-ANP.
<220> FEATURE:
<221> NAME/KEY: primer_bind
<222> LOCATION: (1)..(27)

<400> SEQUENCE: 6
gaattctgag gagattgtag agtcacc                                         27

<210> SEQ ID NO 7
<211> LENGTH: 29
<212> TYPE: DNA
<213> ORGANISM: Artificial Sequence
<220> FEATURE:
<223> OTHER INFORMATION: Primer 5' EcoRI-BRL.
<220> FEATURE:
<221> NAME/KEY: primer_bind
<222> LOCATION: (1)..(29)

<400> SEQUENCE: 7
gaattcgaag atgactgcac gtgacagac                                       29

<210> SEQ ID NO 8
<211> LENGTH: 50
<212> TYPE: DNA
<213> ORGANISM: Artificial Sequence
<220> FEATURE:
<223> OTHER INFORMATION: Primer 3' NotI-BRL-6His.
<220> FEATURE:
<221> NAME/KEY: primer_bind
<222> LOCATION: (1)..(50)

<400> SEQUENCE: 8
gcggccgctt aatgatgatg atgatgatgc ttaattatta taataggtcc                50

<210> SEQ ID NO 9
<211> LENGTH: 133

```
<212> TYPE: PRT
<213> ORGANISM: Homo sapiens
<220> FEATURE:
<221> NAME/KEY: mat_peptide
<222> LOCATION: (1)..(133)

<400> SEQUENCE: 9

Arg Pro Pro Gln Phe Thr Arg Ala Gln Trp Phe Ala Ile Gln His Ile
1               5                   10                  15

Ser Leu Asn Pro Pro Arg Cys Thr Ile Ala Met Arg Ala Ile Asn Asn
            20                  25                  30

Tyr Arg Trp Arg Cys Lys Asn Gln Asn Thr Phe Leu Arg Thr Thr Phe
        35                  40                  45

Ala Asn Val Val Asn Val Cys Gly Asn Gln Ser Ile Arg Cys Pro His
    50                  55                  60

Asn Arg Thr Leu Asn Asn Cys His Arg Ser Arg Phe Arg Val Pro Leu
65                  70                  75                  80

Leu His Cys Asp Leu Ile Asn Pro Gly Ala Gln Asn Ile Ser Asn Cys
            85                  90                  95

Thr Tyr Ala Asp Arg Pro Gly Arg Arg Phe Tyr Val Val Ala Cys Asp
        100                 105                 110

Asn Arg Asp Pro Arg Asp Ser Pro Arg Tyr Pro Val Val Pro Val His
        115                 120                 125

Leu Asp Thr Thr Ile
        130

<210> SEQ ID NO 10
<211> LENGTH: 181
<212> TYPE: PRT
<213> ORGANISM: Artificial Sequence
<220> FEATURE:
<223> OTHER INFORMATION: A novel recombinant protein recombinant
      eosinophil ribonuclease (reRNase) comprising an N-terminal
      39-amino acid artificial peptide and a C-terminal 133-amino acid
      human eosinophil RNase.
<220> FEATURE:
<221> NAME/KEY: MISC_FEATURE
<222> LOCATION: (1)..(181)

<400> SEQUENCE: 10

Met Ser Lys Pro Thr Thr Thr Thr Thr Thr Thr Thr Ala Pro Ser
1               5                   10                  15

Thr Ser Thr Thr Thr Arg Pro Ser Ser Ser Glu Pro Ala Thr Phe Pro
            20                  25                  30

Thr Gly Asp Ser Thr Ile Ser Ser Glu Phe Arg Pro Pro Gln Phe Thr
        35                  40                  45

Arg Ala Gln Trp Phe Ala Ile Gln His Ile Ser Leu Asn Pro Pro Arg
    50                  55                  60

Cys Thr Ile Ala Met Arg Ala Ile Asn Asn Tyr Arg Trp Arg Cys Lys
65                  70                  75                  80

Asn Gln Asn Thr Phe Leu Arg Thr Thr Phe Ala Asn Val Val Asn Val
            85                  90                  95

Cys Gly Asn Gln Ser Ile Arg Cys Pro His Asn Arg Thr Leu Asn Asn
        100                 105                 110

Cys His Arg Ser Arg Phe Arg Val Pro Leu Leu His Cys Asp Leu Ile
        115                 120                 125

Asn Pro Gly Ala Gln Asn Ile Ser Asn Cys Thr Tyr Ala Asp Arg Pro
        130                 135                 140

Gly Arg Arg Phe Tyr Val Val Ala Cys Asp Asn Arg Asp Pro Arg Asp
```

```
                145                 150                 155                 160
Ser Pro Arg Tyr Pro Val Val Pro Val His Leu Asp Thr Thr Ile His
                    165                 170                 175
His His His His His
            180

<210> SEQ ID NO 11
<211> LENGTH: 172
<212> TYPE: PRT
<213> ORGANISM: Artificial Sequence
<220> FEATURE:
<223> OTHER INFORMATION: An alternative kind of reRNase.
<220> FEATURE:
<221> NAME/KEY: MISC_FEATURE
<222> LOCATION: (1)..(172)

<400> SEQUENCE: 11

Ser Lys Pro Thr Thr Thr Thr Thr Thr Thr Thr Ala Pro Ser Thr
1               5                   10                  15

Ser Thr Thr Thr Arg Pro Ser Ser Glu Pro Ala Thr Phe Pro Thr
                20                  25                  30

Gly Asp Ser Thr Ile Ser Ser Arg Pro Pro Gln Phe Thr Arg Ala Gln
            35                  40                  45

Trp Phe Ala Ile Gln His Ile Ser Leu Asn Pro Pro Arg Cys Thr Ile
    50                  55                  60

Ala Met Arg Ala Ile Asn Asn Tyr Arg Trp Arg Cys Lys Asn Gln Asn
65                  70                  75                  80

Thr Phe Leu Arg Thr Thr Phe Ala Asn Val Val Asn Val Cys Gly Asn
                85                  90                  95

Gln Ser Ile Arg Cys Pro His Asn Arg Thr Leu Asn Asn Cys His Arg
            100                 105                 110

Ser Arg Phe Arg Val Pro Leu Leu His Cys Asp Leu Ile Asn Pro Gly
        115                 120                 125

Ala Gln Asn Ile Ser Asn Cys Thr Tyr Ala Asp Arg Pro Gly Arg Arg
    130                 135                 140

Phe Tyr Val Val Ala Cys Asp Asn Arg Asp Pro Arg Asp Ser Pro Arg
145                 150                 155                 160

Tyr Pro Val Val Pro Val His Leu Asp Thr Thr Ile
                165                 170

<210> SEQ ID NO 12
<211> LENGTH: 27
<212> TYPE: DNA
<213> ORGANISM: Artificial Sequence
<220> FEATURE:
<223> OTHER INFORMATION: Primer 5' EcoRI-RNase.
<220> FEATURE:
<221> NAME/KEY: primer_bind
<222> LOCATION: (1)..(27)

<400> SEQUENCE: 12
gaattcagac ccccacagtt tacgagg                                              27

<210> SEQ ID NO 13
<211> LENGTH: 45
<212> TYPE: DNA
<213> ORGANISM: Artificial Sequence
<220> FEATURE:
<223> OTHER INFORMATION: Primer 3' BamHI-RNase-6His.
<220> FEATURE:
<221> NAME/KEY: primer_bind
<222> LOCATION: (1)..(45)
```

<400> SEQUENCE: 13
ggattcttag tggtggtggt ggtggtggat ggtggtatcc aggtg          45

<210> SEQ ID NO 14
<211> LENGTH: 133
<212> TYPE: PRT
<213> ORGANISM: Pan troglodytes
<220> FEATURE:
<221> NAME/KEY: mat_peptide
<222> LOCATION: (1)..(133)

<400> SEQUENCE: 14

```
Arg Pro Pro Gln Phe Thr Arg Ala Gln Trp Phe Ala Ile Gln His Ile
1               5                   10                  15

Ser Leu Asn Pro Pro Arg Cys Thr Ile Ala Met Arg Val Ile Asn Asn
            20                  25                  30

Tyr Arg Trp Arg Cys Lys Asn Gln Asn Thr Phe Leu Arg Thr Thr Phe
        35                  40                  45

Ala Asn Val Val Asn Val Cys Gly Asn Gln Ser Ile Arg Cys Pro His
    50                  55                  60

Asn Arg Thr Leu Asn Asn Cys His Gln Ser Arg Phe Arg Val Pro Leu
65                  70                  75                  80

Leu His Cys Asp Leu Ile Asn Pro Gly Ala Gln Asn Ile Ser Asn Cys
                85                  90                  95

Arg Tyr Ala Asp Arg Pro Gly Arg Arg Phe Tyr Val Val Ala Cys Asp
            100                 105                 110

Asn Arg Asp Pro Arg Asp Ser Pro Arg Tyr Pro Val Val Pro Val His
        115                 120                 125

Leu Asp Ala Thr Ile
    130
```

<210> SEQ ID NO 15
<211> LENGTH: 133
<212> TYPE: PRT
<213> ORGANISM: Gorilla gorilla
<220> FEATURE:
<221> NAME/KEY: mat_peptide
<222> LOCATION: (1)..(133)

<400> SEQUENCE: 15

```
Arg Pro Pro Gln Phe Thr Arg Ala Gln Trp Phe Ala Ile Gln His Ile
1               5                   10                  15

Ser Leu Asn Pro Pro Arg Cys Thr Ile Ala Met Arg Val Ile Asn Asn
            20                  25                  30

Tyr Arg Trp Arg Cys Lys Asn Gln Asn Thr Phe Leu Arg Thr Thr Phe
        35                  40                  45

Ala Asn Val Val Asn Val Cys Gly Asn Gln Ser Ile Arg Cys Leu His
    50                  55                  60

Asn Arg Thr Leu Asn Asn Cys His Arg Ser Arg Phe Arg Val Pro Leu
65                  70                  75                  80

Leu His Cys Asp Leu Ile Asn Pro Gly Ala Gln Asn Ile Ser Asn Cys
                85                  90                  95

Arg Tyr Ala Asp Arg Pro Gly Arg Arg Phe Tyr Val Val Ala Cys Asp
            100                 105                 110

Asn Arg Asp Pro Gln Asp Ser Pro Arg Tyr Pro Val Val Pro Val His
        115                 120                 125

Leu Asp Thr Thr Ile
```

```
<210> SEQ ID NO 16
<211> LENGTH: 133
<212> TYPE: PRT
<213> ORGANISM: Macaca fascicularis
<220> FEATURE:
<221> NAME/KEY: mat_peptide
<222> LOCATION: (1)..(133)

<400> SEQUENCE: 16
```

Arg Pro Pro Gln Phe Thr Lys Ala Gln Trp Phe Ala Ile Gln His Ile
1               5                   10                  15

Asn Val Asn Pro Pro Arg Cys Thr Ile Ala Met Arg Val Ile Asn Asn
            20                  25                  30

Tyr Gln Arg Arg Cys Lys Asn Gln Asn Thr Phe Leu Arg Thr Thr Phe
        35                  40                  45

Ala Tyr Thr Ala Asn Val Cys Arg Asn Glu Arg Ile Arg Cys Pro Arg
    50                  55                  60

Asn Arg Thr Leu His Asn Cys His Arg Ser Arg Tyr Arg Val Pro Leu
65                  70                  75                  80

Leu His Cys Asp Leu Ile Asn Pro Gly Ala Gln Asn Ile Ser Thr Cys
                85                  90                  95

Arg Tyr Ala Asp Arg Pro Gly Arg Arg Phe Tyr Val Val Ala Cys Glu
            100                 105                 110

Ser Arg Asp Pro Arg Asp Ser Pro Arg Tyr Pro Val Val Pro Val His
        115                 120                 125

Leu Asp Thr Thr Ile
    130

```
<210> SEQ ID NO 17
<211> LENGTH: 133
<212> TYPE: PRT
<213> ORGANISM: Macaca nemestrina
<220> FEATURE:
<221> NAME/KEY: mat_peptide
<222> LOCATION: (1)..(133)

<400> SEQUENCE: 17
```

Arg Pro Pro Gln Phe Thr Lys Ala Gln Trp Phe Ala Ile Gln His Ile
1               5                   10                  15

Asn Val Asn Pro Pro Arg Cys Thr Ile Ala Met Arg Val Ile Asn Asn
            20                  25                  30

Tyr Gln Arg Arg Cys Lys Asn Gln Asn Thr Phe Leu Arg Thr Thr Phe
        35                  40                  45

Ala Asn Thr Val Asn Val Cys Arg Asn Arg Ser Ile Arg Cys Pro Arg
    50                  55                  60

Asn Arg Thr Leu His Asn Cys His Arg Ser Ser Tyr Arg Val Pro Leu
65                  70                  75                  80

Leu His Cys Asp Leu Ile Asn Pro Gly Ala Gln Asn Ile Ser Thr Cys
                85                  90                  95

Arg Tyr Ala Asp Arg Pro Gly Arg Arg Phe Tyr Val Val Ala Cys Glu
            100                 105                 110

Ser Arg Asp Pro Arg Asp Ser Pro Arg Tyr Pro Val Val Pro Val His
        115                 120                 125

Leu Asp Thr Ile Ile
    130

```
<210> SEQ ID NO 18
<211> LENGTH: 133
<212> TYPE: PRT
<213> ORGANISM: Pongo pygmaeus
<220> FEATURE:
<221> NAME/KEY: mat_peptide
<222> LOCATION: (1)..(133)

<400> SEQUENCE: 18

Lys Pro Arg Gln Phe Thr Arg Ala Gln Trp Phe Ala Ile Gln His Val
1               5                   10                  15

Ser Leu Asn Pro Pro Gln Cys Thr Thr Ala Met Arg Val Ile Asn Asn
            20                  25                  30

Tyr Gln Arg Arg Cys Lys Asp Gln Asn Thr Phe Leu Arg Thr Thr Phe
        35                  40                  45

Ala Asn Val Val Asn Val Cys Gly Asn Pro Asn Ile Thr Cys Pro Arg
    50                  55                  60

Asn Arg Thr Leu His Asn Cys His Arg Ser Arg Phe Gln Val Pro Leu
65                  70                  75                  80

Leu His Cys Asn Leu Thr Asn Pro Gly Ala Gln Asn Ile Ser Asn Cys
            85                  90                  95

Lys Tyr Ala Asp Arg Thr Glu Arg Phe Tyr Val Val Ala Cys Asp
            100                 105                 110

Asn Arg Asp Pro Arg Asp Ser Pro Arg Tyr Pro Val Val Pro Val His
            115                 120                 125

Leu Asp Thr Thr Ile
            130
```